United States Patent [19]
Weber et al.

[11] Patent Number: 5,273,765
[45] Date of Patent: Dec. 28, 1993

[54] INITIATING A RESPONSE SIGNAL TO A PREDETERMINED PROCESSING CONDITION

[75] Inventors: Mark J. Weber, Marshfield; Marc A. Winzenried, Dorchester, both of Wis.

[73] Assignee: ESE, Inc., Marshfield, Wis.

[21] Appl. No.: 16,050

[22] Filed: Feb. 10, 1993

[51] Int. Cl.⁵ ............................................. G01N 25/00
[52] U.S. Cl. ............................... 426/231; 73/64.41; 426/36; 426/233
[58] Field of Search ................ 426/231, 233, 36, 582; 73/64.41; 374/21, 43

[56] References Cited

U.S. PATENT DOCUMENTS

| | | | |
|---|---|---|---|
| 3,366,942 | 1/1968 | Deane | 340/243 |
| 3,453,864 | 7/1969 | Chiu | 73/15 |
| 3,821,643 | 6/1974 | Bostick et al. | 324/65 R |
| 3,840,806 | 10/1974 | Stoner et al. | 324/65 R |
| 3,898,638 | 8/1975 | Deane et al. | 340/243 |
| 3,899,595 | 8/1975 | Stenne | 426/36 |
| 4,059,006 | 11/1977 | Mizutani et al. | 73/17 A |
| 4,244,217 | 1/1981 | Ledbetter | 73/204 |
| 4,484,821 | 11/1984 | Willcock | 374/24 |
| 4,501,145 | 2/1985 | Boegli et al. | 73/204 |
| 4,512,182 | 4/1985 | Rizvi et al. | 73/64 |
| 4,542,645 | 9/1989 | Richardson et al. | 73/64.1 |
| 4,578,988 | 4/1986 | Hori et al. | 73/54 |
| 4,611,928 | 9/1986 | Hori et al. | 374/21 |
| 4,663,169 | 5/1987 | Hori et al. | 426/38 |
| 4,781,469 | 11/1988 | Turon-Lagot | 374/27 |
| 5,014,553 | 5/1991 | Hori et al. | 73/295 |

Primary Examiner—George Yeung
Attorney, Agent, or Firm—M. Paul Hendrickson

[57] ABSTRACT

The present invention provides a method for initiating a responsive signal to a predetermined processing condition. The method relies upon generating sufficient processing data about a desired processing condition to establish a processing profile reflective of the condition. The predetermined processing condition is indexed or inputted onto the profile which, in turn, allows for automatically initiating the signal when subsequent processes achieve the indexed condition. The method is particularly applicable for determining a proper curding point in a cheese manufacture using a control computer to store and compare an indexed processing profile with an on-going plant run.

20 Claims, 5 Drawing Sheets

FIG. 6
(LEARN)
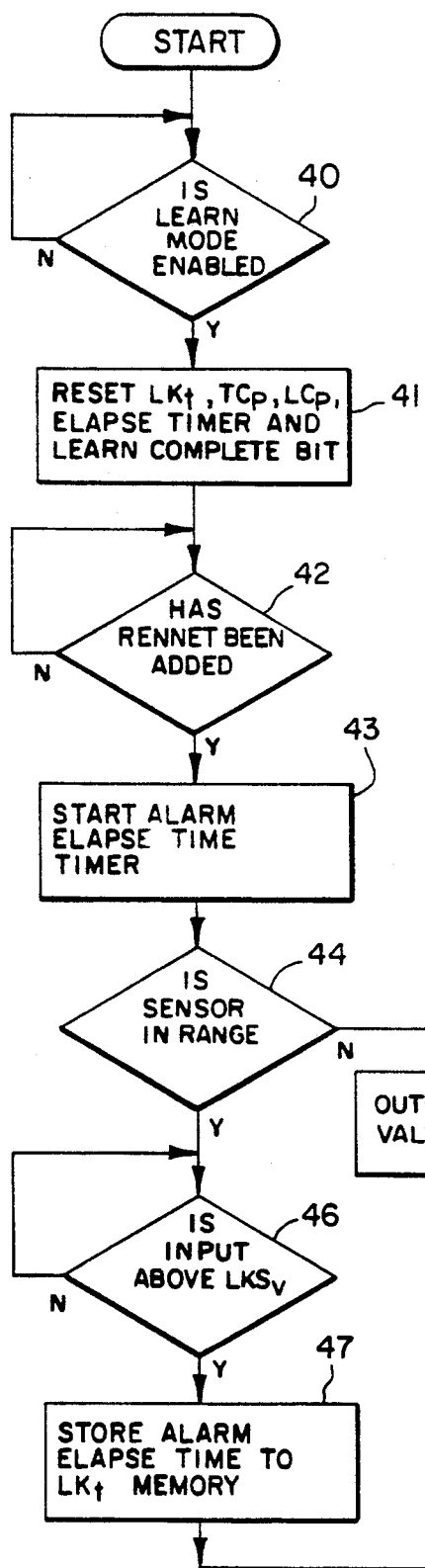
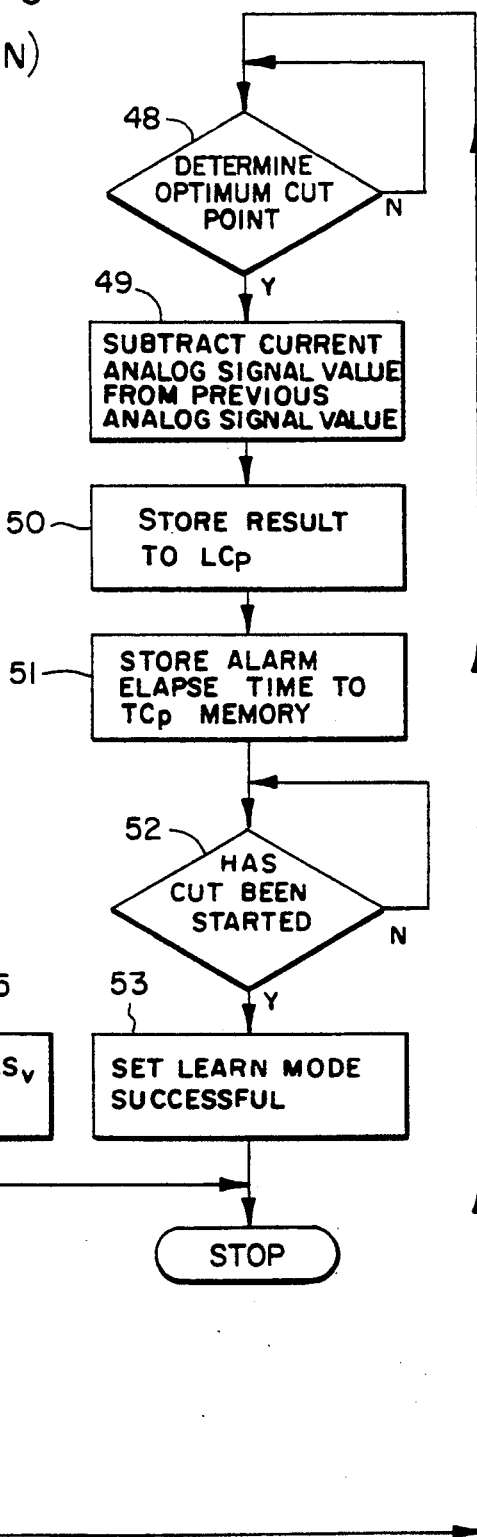

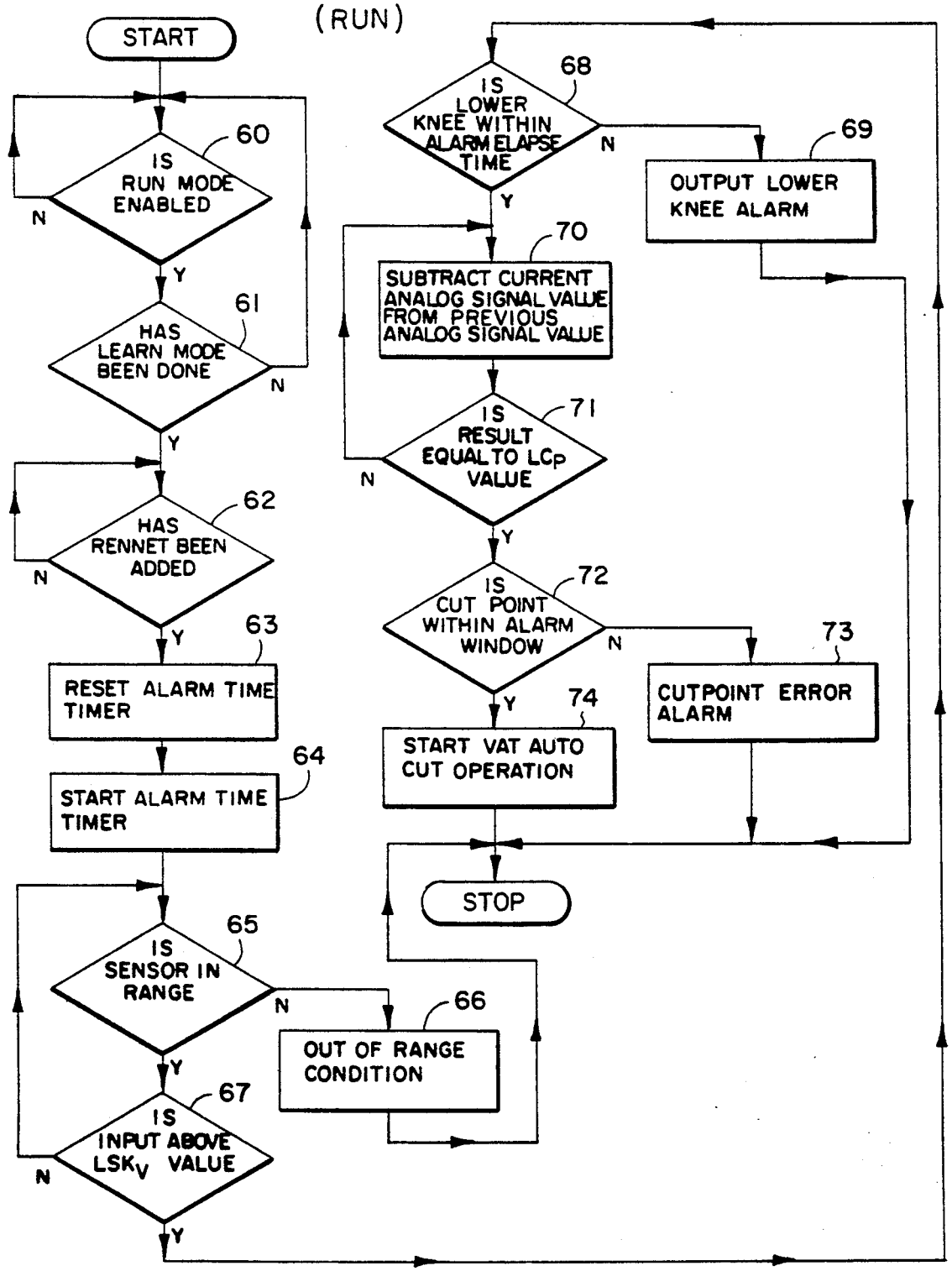

INITIATING A RESPONSE SIGNAL TO A PREDETERMINED PROCESSING CONDITION

FIELD OF THE INVENTION

The present invention relates to control systems for solidification processes and more particularly a system and method for signaling a predetermined stage in a solidification or coagulation process.

BACKGROUND OF THE INVENTION

Scores of different cheeses are manufactured by the cheese industry. The ingredients of the recipe typically include milk, microorganisms as a starter, rennet, and salt. The cheese flavor, texture and body often hinges upon the particular preferences of the cheese maker. A basic cheese recipe typically entails adding a starter culture (a microorganism) to the milk, allowing the milk to coagulate with or without rennet, and then draining off the whey with or without aging to develop cheese flavor, texture and body.

Cheese manufacture includes the acid curd cheeses typically made by coagulating milk with acid forming starters or cultures and the rennet curd cheeses made by coagulating milk with rennet. The starter favors lactic acid formation which coagulates the milk and hastens coagulation by the rennet. Rennet favors expulsion of whey and fusion of curd particles. In the cheese manufacture, the coagulating milk reaches a condition the cheese maker considers to be an optimum curding point, at which processing stage the cheese coagulum is often curded into small cubes by cutting with a meshed wire followed by draining the whey from the cheese vat to provide what is often referred to as cheese curds or a curded cheese product. The cheese curds are quite resilient and may be compressed or molded into the desired cheese bricks. Each cheese maker practices certain techniques, including when to curd, which contribute unique flavoring or textural character to the cheese.

Cheese making is an art. Cheese makers are skilled artisans who rely upon a host of objective and subjective recipe criteria designed to consistently replicate a cheese product of a well defined flavor, texture, body and consumer acceptability. Several hundred different kinds of cheese may be made from essentially the same ingredients simply by slightly varying the processing conditions. Each cheese maker, however, strives to consistently replicate a successful "in house" cheese recipe. Small recipe deviations can result in substantial departures from the desired end product. Sophisticated cheese consumers can often detect minor variations in flavor, texture, or body in a favorite cheese product. Cheese makers will often physically touch the cheese coagulum for purposes of ascertaining a proper curding stage.

An important decision in the cheese manufacture pertains to the optimum processing stage to cut or curd the cheese coagulum. Curding at what is considered to be an optimum curding point facilitates standardization in quality control and replication of the desired cheese end product. Failure to curd at the appropriate coagulation stage can lead to a cheese product substantially different in product identity from what was intended. Reproduction of the cheese recipe is essential to maintaining consumer acceptance and allegiance to any given cheese product.

There have been numerous attempts to instrumentally or analytically determine when a coagulum may be cut in a cheese manufacture. These attempts have not been entirely successful. Representative patents relying upon instruments to determine curding or cutting of coagulum in cheese making include U.S. Pat. Nos. 4,578,988; 4,611,928; 4,663,169; and 5,014,553. These patents collectively rely upon heating a thin metal wire with an electric current and monitoring the wire temperature for purposes of establishing a theoretical cutting point. These determinations rely upon extensive experimentation and correlation of accumulated data generated by a specific thin metal wire detector in a specific cheese coagulation and complex theoretical calculations and derivations derived from the accumulated data.

The use of a thin metal wire equipped with current feeding and voltage measuring terminals to determine the development of coagulum in a cheese making process is reportedly a complex and tedious task. The determination reportedly requires numerous plant runs to establish sufficient information for the calibration of the instrumentation and to compensate for inherent variations in the detected responses from the actual condition or actual state of the coagulum. Calibration of the equipment to the cheese making process requires tedious examination of the data and restructuring of the data in an attempt to establish what the calibrators consider to be optimum cheese curding time. If the "optimum cheese curding time" of the process calibrator fails to meet the cheese maker's desired cutting time, additional testing and data is generally required to recalibrate the cutting time.

There exists a need for a means to empirically determine by a cheese maker an optimum cheese curding stage in an automated curding in cheese manufacture. There exists a need for instrumentation which more precisely and accurately determines when a coagulating milk mass converts to a coagulated cheese product suitable for curding as empirically sought by the cheese maker. There exists a need for an accurate profile for tracking the thermal conductivity of a coagulating milk mass in a cheese manufacture which allows the cheese maker to determine precisely at what stage within the tracked profile the cutting of the cheese coagulum should occur.

It would be particularly beneficial to be able to record and store a composite profile of cheese coagulation processes in a conventional computer database and enable the cheese maker to select at that particular processing stage or juncture of the profile for curding the cheese coagulum. If these needs could be fulfilled, an ordinary worker would be able to replicate the empirical artfulness of a master cheese maker. Such a system would also allow the cheese industry to more consistently replicate the desired end product.

SUMMARY OF THE INVENTION

The present invention provides a method for initiating a responsive signal (e.g. such as a signal to commence cheese curding) to a predetermined change in a solidification process. The method may be applied to cheese making and affords a simple and accurate method for determining the most appropriate stage for cutting a cheese curd. The method permits the cheese maker to empirically establish and record for future use a processing stage for curding the cheese. This determination may be made upon the basis of one or more standardization runs which, in essence, establishes a thermal conductivity or sensing temperature profile or composite profile for a given or specific cheese type in a cheese manufacture.

Storing of the thermal conductivity profile in a memory means or unit provides a database for monitoring and regulating the future processing of the coagulation of milk to a cheese coagulum. The stored profile is indexed by empirically observing a coagulating process (while sending thermal conductivity data thereof to the memory unit) and indexing the data sent to the memory unit of the optimum processing stage to "curd" the cheese coagulum. The stored thermal conductivity profile indexed with the optimum cheese curding stage provides a data base for initiating a responsive signal (e.g. stage to curd the cheese) in all subsequent runs of the cheese coagulation process. In future coagulating runs, the thermal conductivity data thereof is sent to the memory unit which compares the sent data to the stored and indexed profile. When the coagulum data reaches the indexed level, initiating the responsive signal can, for example, automatically start the cheese cutters.

The thermal conductivity profile and data for coagulating milk masses may be effectively and accurately obtained by comparatively measuring the electrical output of two heat sensing probes in a prearranged spatial arrangement to a heat source and immersed in the coagulating milk. The heat sensing probes are spaced at different distances from the heat source. When the media comprises a fluid such as fluid milk, little, if any, detected differences between the output of the two sensors will be observed. As the fluid converts from a liquid to a semi-solid to a solid mass, the solidifying mass creates an increasing thermal barrier against dissipation of heat about the heater. One of the heat sensors (a reference and distal sensor) remains substantially unaffected by heat generated by the heater since it is insulated by the coagulating mass. The other thermal sensor in closest proximity (proximate or active sensor) to the heat source, however, serves as a thermal conduit for dissipating heat generated by the heat source. Heating the closest heat detecting sensor results in an increase in its electrical resistance. In contrast, the furthest removed sensor is well insulated by the coagulating mass and removed from the heat source and, accordingly, its electrical resistance changes little, if any, from its initial resistance when the mass was in the fluid state. The heat sensing system includes means for comparing the output signals of the heat sensors and amplifying the comparative differences into an electronic signal for relaying and storing in a memory unit.

In operation, the aforementioned heat sensors may be used as part of a wheatstone bridge comprised of the two sensors, two fixed resistors and a variable resistor. As the coagulating liquid becomes less fluid, the electrical resistance of the proximate sensor becomes significantly greater than that of the reference sensor which, in turn, upsets the balance of the wheatstone bridge and, thereby, increases the millivolt output at the active sensor side of the wheatstone bridge. The output is continuously amplified and recorded in a memory unit. The output recorded in the memory unit creates a profile of the thermal conductivity of the coagulating mass in the cheese manufacture.

The present process possesses a high order of resolution and reproducibility for any given type of cheese manufacture. The cheese maker needs only to empirically index upon the profile the optimum processing stage when the coagulated cheese should be cut for any given cheese manufacture type. When the output of the ongoing cheese process matches onto the stored graphic profile and index, the cheese coagulum is ready for cheese curding. Once the expert cheese maker has established or tagged the profile for cutting in an established data bank, a novice can thereafter accurately rely upon present method to determine the appropriate stage to cut the cheese coagulum and thereby substantially duplicate that of the cheese maker.

BRIEF DESCRIPTION OF THE DRAWINGS

FIG. 6 depicts a flow sheet of central computer software in a learning mode of operation adapted for use in a cheese manufacture.

FIG. 7 depicts a flow sheet for central computer software in an operational mode.

DETAILED DESCRIPTION OF THE INVENTION

According to the present invention there is provided a method for initiating a responsive signal to a predetermined change of a solidifying liquid converting from a liquid to a solid, said method comprising:

a) storing in a memory unit at least one thermal conductivity profile of the solidifying liquid;

b) indexing upon said profile by physical observation an activating threshold indicative of said predetermined change;

c) conducting a subsequent liquid solidification while sending thermal conductivity data of said subsequent liquid solidification to the memory unit;

d) comparing said profile in said memory to said data until said data reaches the activating threshold; and e) initiating a responsive signal upon achievement of said threshold and thereby providing the responsive signal to said predetermined change.

The determination method of this invention may be used to monitor a wide variety of solidification processes involving the conversion of a fluid to a solid and vice versa. The method is particularly well suited for adaptation to fermentation processes involving the coagulation of a liquid to a solid and especially in the coagulation of milk to cheese. The method allows for recording in a memory means a standardized profile of the process and an empirical observation for signaling a desired predetermined change in the solidification process.

The predetermined change may represent any stage or juncture for altering or modifying the solidification process. The predetermined change may signal the need to conduct a certain processing function at a crucial processing stages such as introducing a chemical, a reactant, a catalyst, a biochemical, an enzyme, a microbial reagent, a diluent, solvent or other additive or adjunct to the process, to alter the processing conditions such as changing the pH, temperature, concentration, pressure, etc., engaging processing equipment such as starting a pump, a stirrer, cheese cutters, heat exchangers, evaporators, etc. The predetermined change may be indexed onto the processing profile for any desired purpose and processing stage of the solidification process.

The need for initiating a responsive signal to a predetermined change in a coagulation process may be illustrated by the preferred adaptation of the present method to a cheese manufacture in which milk is coagulated to a cheese coagulum. The desired response to a predetermined processing change may represent a responsive signal such as a relaying or switching means for starting the cheese cutting or curding equipment (e.g. electric motors) to curd the cheese coagulum at an optimum cheese curding processing stage.

Figure 1:
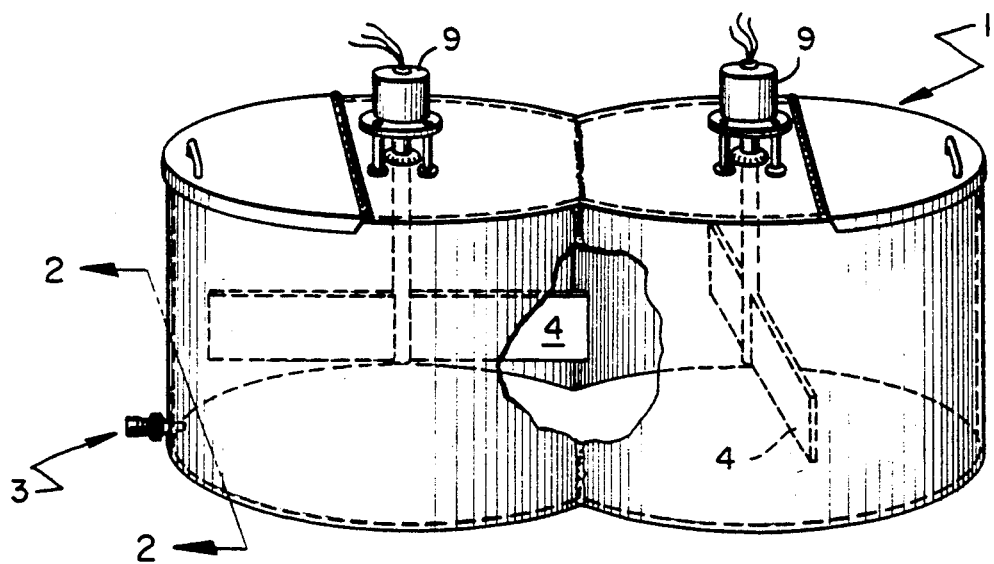
FIG. 1 is a view depicting a vat equipped with a sensory system for detecting physical changes in materials being processed within the vat.
Figure 8:
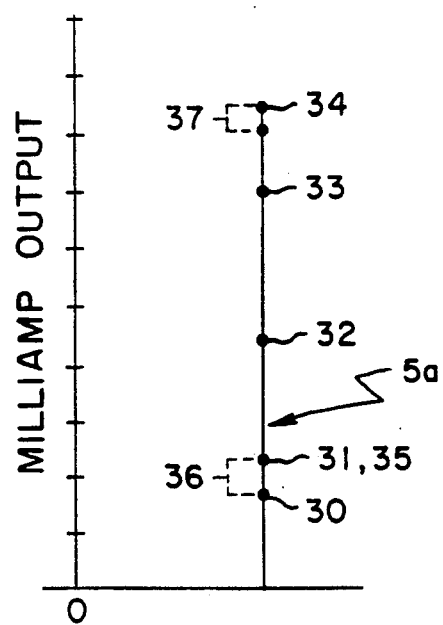
FIG. 8 depicts an alternative profile for the electronic output of FIG. 5 in a cheese manufacture.
Figure 4:
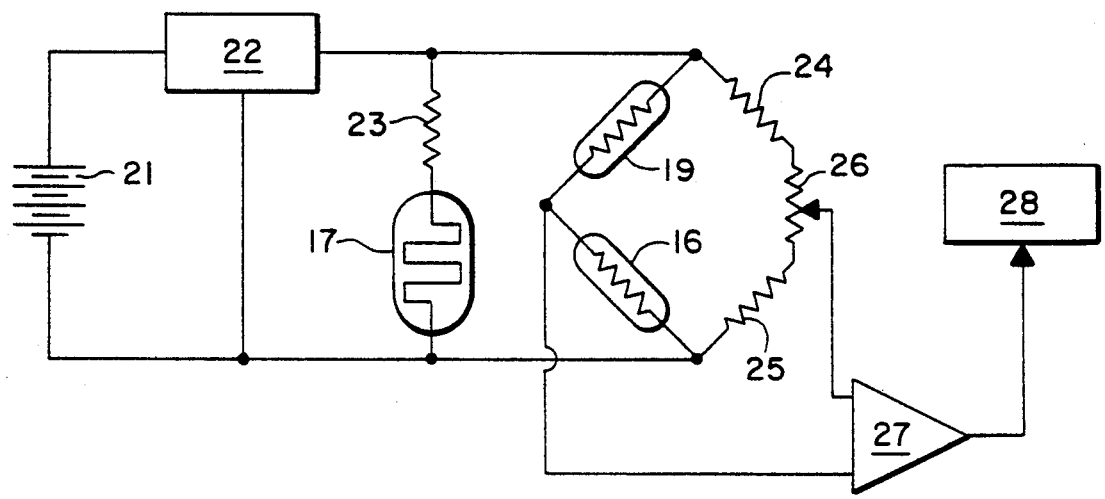
FIG. 4 is a schematic diagram of an electrical circuit for detecting the physical changes with the sensory system depicted by FIGS. 1-3.
Figure 5:
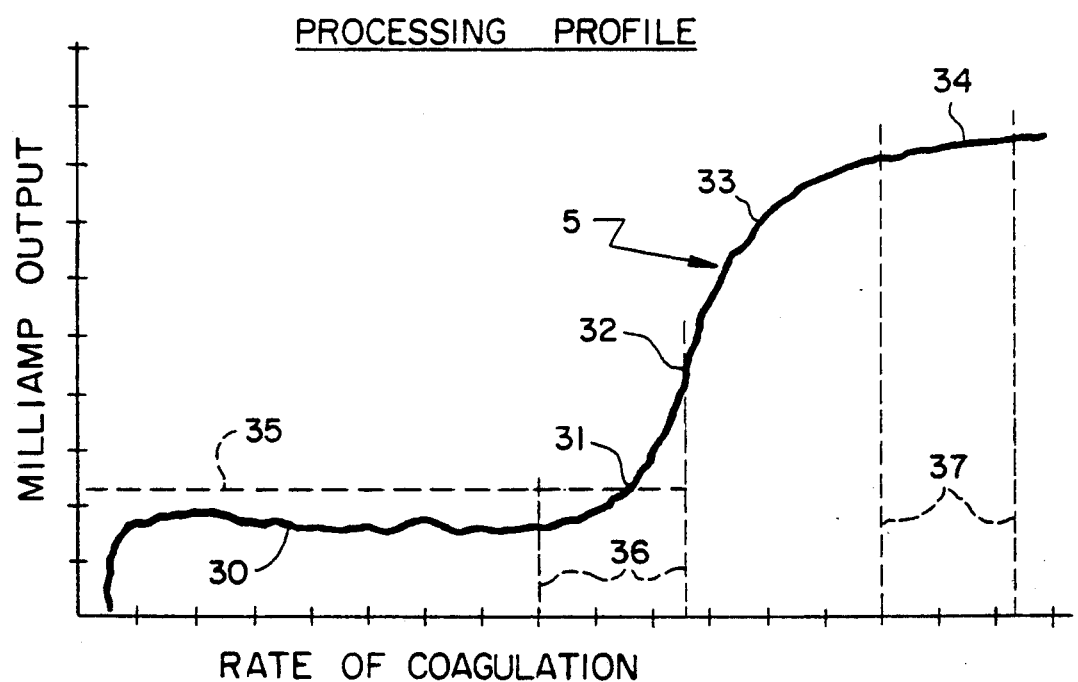
FIG. 5 graphically profiles the electronic output of the sensory system and circuitry of FIG. 4 indexed so as to initiate a responsive signal to a predetermined change in a cheese manufacture.

FIG. 1 illustrates a vat (generally designated as 1) equipped with a sensory system 3 for detecting physical changes (e.g. such as the thermal conductivity data as graphically profiled in the processing profile 5 of FIGS. 5 and 8) occurring to vatted and coagulating milk mass in a cheese manufacture. Vat 1 for simplistic and illustrative purposes is shown as including a pair of blades 4 (which serve to stir in one direction and cut by reversing blades 4) powered by reversible electric motors 9. These physical changes may be continuously inputted to a memory means 28 of FIG. 4 (e.g. a data bank or memory unit) so as to provide a processing profile (generally prefixed by 5 as illustrated in FIGS. 5 or 8) of the milk converting to the desired cheese coagulum for a particular cheese recipe. The processing profile 5 may typically represent the thermal conductivity profile or temperature profile of the cheese manufacture using the determination method of this invention. The profiles 5 and 5a and the desired juncture of an activating threshold (represented as 34 in FIGS. 5 and 8) for initiating a responsive signal to a predetermined change 34 are generally uniquely applicable to the particular cheese making recipe of the manufacture. Thus the predetermined change 34 indexed to profiles 5 and 5a may empirically differ from recipe to recipe and depends largely upon the operating cheese maker's choice. The determination allows an expert cheese maker to record the pertinent profiles 5 and 5a and pertinent predetermined change 34 (e.g. optimum cheese curding stage) as it applies to the unique or particular recipe of the cheese manufacturer.

Figure 3:
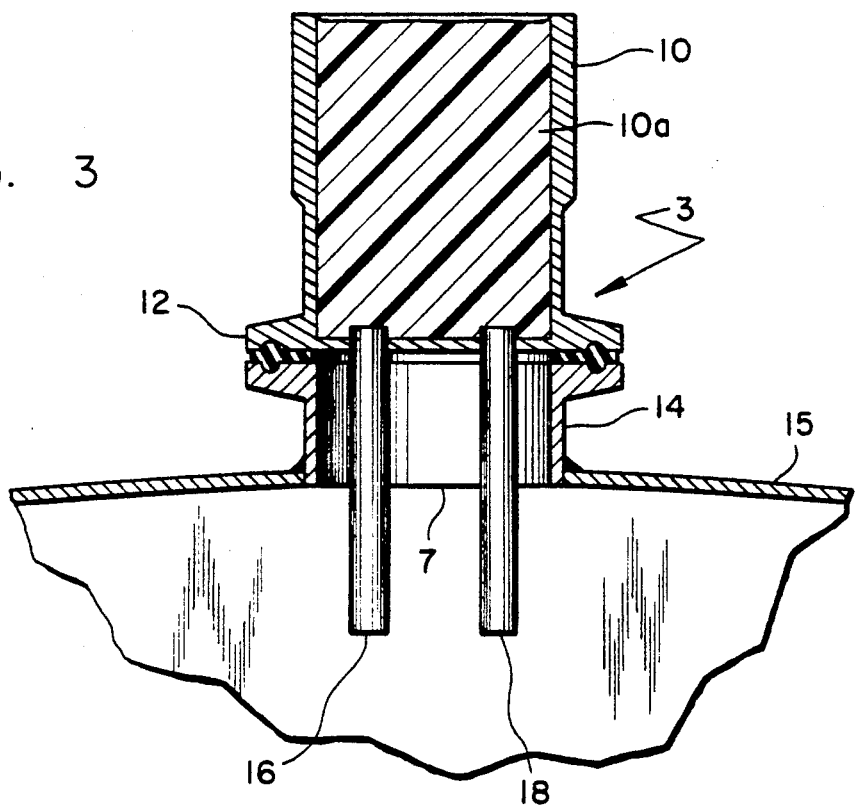
FIG. 3 is a view taken along line 3—3 of FIG. 2.
Figure 2:
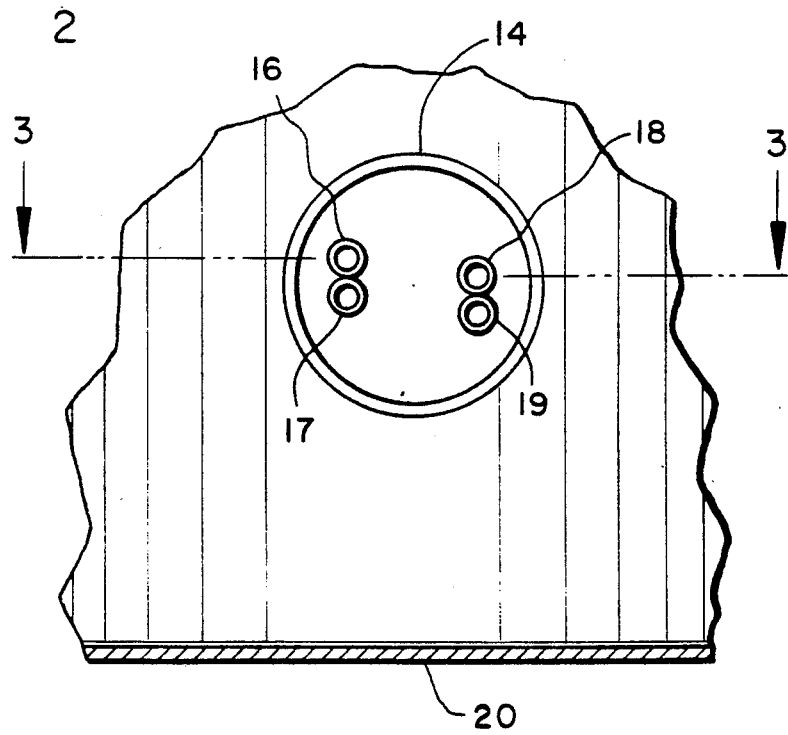
FIG. 2 is a view taken along line 2—2 of FIG. 1.

FIGS. 2 and 3 depict an enlarged view of the probe assembly 3 respectively taken along line 2—2 of FIG. 1 and line 3—3 of FIG. 2. In cheese manufacture and other food processes, the equipment and components directly contacting onto the processed materials should be of a sanitary design and construction. The probe assembly 3 for monitoring the process is preferably installed onto the vat sidewall 15 near the bottom 20 of the cheese vat 1. Conventional cheese vats 1 may be adapted to receive probe assembly 3 by simply cutting or drilling a port hole 7 and welding the sanitary type fitting 14 to port hole 7 as depicted by FIG. 3. The probe assembly 3 includes four tubular probing tips 16-19 which are positioned by port fitting 14 to protrude into the vat 1 as far as possible while still allowing sufficient clearance to clear any internal rotating or moving mechanical equipment (e.g. blades 4) of vat 1.

A particularly effective and reliable probe assembly 3 for installation and use in the present method is a model 8-66 MPS Point Kit Assembly, manufactured and distributed by Fluid Components, Inc. (FCI), 1755 La Costa Medous Drive, San Marcos, Calif. 92069. The model 8-66 MPS probe assembly 3 includes the electronic components 22-26 of FIG. 4, with the furnished transformer being removed from probe assembly 3. U.S. Pat. Nos. 3,366,942 and 3,898,638 to Dean et al and a Fluid Components, Inc. publications identified as Doc. Nos. 3027, No. 11037B, 11055B, and 11041B (incorporated by references herein) may be referred to for further information concerning the probe assembly 3 of the type depicted in FIGS. 2 and 3.

The sensing assembly 3 detailed by FIGS. 2-4 include four, rigid, small diameter, equally sized, tubular casings 16-19 which extend outwardly from the probe base 12 into vat 1. The sensing assembly 3 is designed and constructed so as to operationally provide reliable and accurate data as to the physical condition or state of the processed materials at any given processing stage. Two of the tubes depicted as 16 and 19 house heat sensors (represented as resistors 16 and 19 in FIG. 4) which cooperatively readily and accurately detect minute changes in the liquidity of the processing materials. The four tubes 16-19 comprise an active sensor 16 and heater 17 combination, and a dummy casing 18 and reference sensor 19 combination. The sensing efficacy of sensors 16 and 19 is enhanced by properly orienting tubes 16-19 as shown in FIG. 2. As may be observed from FIG. 2, the active sensor 16 and heater 17 combination are vertically aligned onto one side and the dummy casing 18 and reference sensor 19 combination are vertically aligned to one another on the opposite side. The orientation should place the center of the active sensor 16 and the heater 17 in vertical alignment.

Sensors 16 and 19 represent a matched pair of conventional resistance thermal detector elements (as depicted in FIG. 4) with a high positive temperature coefficient of resistance. Sensors 16 and 19 are hermetically jacketed within a thin walled stainless steel jacket of a high thermal conductivity and resistivity to high temperatures and chemicals.

Dummy probe 18 and heater 17 are likewise jacketed by a thin walled stainless steel jacket which replicates the jacketed construction and configuration of the sensor 16 and 19 jackets. Heater 17 includes a conventional heating type element such as illustrated by FIG. 4. The dummy probe 18 and the heater with reference sensor 19 combination replicates the mass, thermal flow dynamics and configuration of the active sensor 16 and heater 17 combination. The replication equilibrates the two combinations so as to effectively sense temperature differences between sensors 16 and 18 with a greater degree of accuracy and sensitivity. The probe case 10 is internally filled with an epoxy type material 10a to minimize moisture contamination and mechanical failure of the probe internal components.

As may be partially observed from FIG. 2, the jacketed active sensor 16 and jacketed heater 17 are tangentially contacted (welded) to each other along their major cylindrical axis as are also the reference sensor 19 and dummy probe 18. In a liquid medium, the liquid readily conducts and transfers heat away from heater 17 to the liquid. As the mass solidifies, the solidifying mass insulates heater 17 against heat transfer therefrom. Consequently, the active sensor 16 serves to sense the accumulating and undissipated heat about sensor 16. The reference sensor 19 is spatially separated from the heater 17 at a sufficient distance to minimize a heating effect of heater 17 thereupon. Thus, the reference sensor 19 and dummy casing 18 remain insulated against thermal increases about heater 17 by the test media and generally unaffected by the solidification thereof.

Referring to FIG. 4, the depicted circuit includes a DC power source 21 with a DC voltage regulator 22 for supplying a constant voltage to heater 17. The current flow to heater 17 is separated from the current flow to sensors 16 and 19. A fixed resistor 23 is used to limit the current supply to heater 17 and to minimize the heating effect upon reference sensor 19. The reference sensor 19 and active sensor 16 are part of the wheatstone bridge arrangement of probe assembly 3 as depicted in FIG. 4. This arrangement of probe assembly 3 includes the active sensor 16, the reference sensor 19, two fixed resistors 24 and 25, and a variable resistor 26. The variable resistor 26 serves to equalize or balance current flow between the bridge when probes 16 and 19 are immersed into the coagulating liquid at the processing temperature. The differential amplifier 27 converts the millivolt signal output from the wheatstone bridge consisting of components 16, 19, 24, 25 and 26 to a high level milliamp signal for processing by control computer 28.

In operation, electrical outputs from resistors 24 and 25 are balanced by adjusting variable resistor 26 to a value of 10 percent over the zero point as defined by the output of the differential amplifier 27 (e.g. such as differential amplifier Model No. 4010 GD-24, produced and distributed by Absolute Process Instruments) to the input into the control computer 28 (e.g. Allen Bradley PLC Model SLC-502). During the cheese making process, the heater 17 continuously emits heat which the fluid milk readily conducts away from heater 17. The liquid milk possesses a sufficiently high thermal conductivity so that substantially all of the heat generated by the heater 17 is thermally conducted away from the heater 17. The high thermal conductivity of the liquid milk is also typified by the relatively low milliamp output of differentiated amplifier 27 as represented by point 30 of the processing profiles 5 and 5a. Point 30 of FIG. 5 represents an appropriate processing juncture for adjusting variable resistor 26 of FIG. 4 to a millivolt output at the differential amplifier 27 amounting to about 10 percent over the lower threshold of point 30 of FIG. 5.

As may be observed from the processing profile of FIG. 5, the coagulation of the milk causes the coagulating milk to become less thermally conductive. This results in heat generated about the heater 17 to be sensed by active sensor 16 as evidenced by the progressive increase in milliamp output at point 31 of FIG. 5 and thereafter. As the temperature sensed by the active sensor 16 increases, electrical resistance within sensor 16 increases. The increased resistance of sensor 16 upsets the electrical balance of the wheatstone bridge which further increases the millivolt signal to the differential amplifier 27. The gain of the differential amplifier 27 should also be adjusted so the maximum input to the differential amplifier 27 produces an output amounting to about 90 percent of the maximum input to the control computer 28.

The profiles 5 and 5a of FIGS. 5 and 8 depict the thermal conductivity profiles 5 of a coagulating milk before and after the rennet (point 30) has been added to the cheese vat 1 as monitored by the probe assembly 3.

The milliamp output illustrated in FIG. 5 includes a series of small up and down swings about point 30 which typically arise because of slight movement of milk in vat 1. As the milk initially starts to coagulate, a slight movement or inflection occurs as indicated at number 31 of profile 5 after which the output starts to stabilize. The coagulating milk becomes less thermally conductive as it converts to cheese. This increasingly unbalances the current flow through the wheatstone bridge and rapidly increases the milliamp output of amplifier 27 as may be observed by comparing the curve bridging between point 31 and point 33. Point 34 represents the desired empirical processing stage for curding or cutting the cheese as empirically determined by a cheese maker. Point 34 thus represents what may be referred to as an activating threshold indicative of a predetermined change for activating a responsive signal. The profile 5 curvature bridging region 37 of FIG. 5 represents a check point inputted into the learn mode of FIG. 6 as a window and alarm check for insuring the operational curd determination of point 34 occurs within the appropriate region of profile 5.

The control computer 28 comprises the memory unit which, is programmed for two modes, namely a learn and run mode as shown in FIGS. 6 and 7. The learn mode is detailed in FIG. 6 while the run or operating mode is illustrated by FIG. 7. The abbreviations depicted in the flow charts of FIGS. 6 and 7 are as follows: LKSv=Curve Lower Knee Set Value; LKt=Curve Lower Knee Elapse Time Value; TCp=Cut Point Elapse Time Value; and LCp=Cut Point Level Analog Value.

In the preferred embodiments of the invention, the learn mode of FIG. 6 should be successfully completed before commencing the operational use of the run mode of FIG. 7. Both modes include a conditioner to filter the milliamp output of the differential amplifier 27 through a software averager to remove output spikes or abnormalities such as large changes in output. During operation, both modes monitor milliamp output for any significant deviation which may indicate an abnormality from normal output and profile. If, during any operation a monitoring abnormality is observed to which an alarm is generated, the control computer 28 will then abort the process.

The flow chart of FIG. 6 depicts the control computer 28 operating in a learn mode. The learn mode is typically used by the operating customer (e.g. by a cheese maker) for indexing an activating index representative of a desired predetermined change to be signaled during a particular processing stage in a manufacturing process, such as an optimum desired cut point in a cheese manufacture. Once the cut point has been learned and indexed upon the learn mode, inexperienced operators in a cheese making process can consistently make accurate cuts.

The learn mode is selected by the operator at step 40. Step 41 is used to reset all learn mode parameters. Step 42 awaits for the operator to add the rennet to the vatted milk. After the rennet addition, the alarm timer 43 is started.

The process value of this timer 43 is stored at the start of the coagulation 31 and at the desired cut point 34 as depicted in FIG. 5. The alarm time value is stored to check the start of coagulation 31 and that the cut point 34 occur within a reasonable time window as illustrated by the profile points between 36 and 37 of FIG. 5.

The inputted data for the FIG. 6 learn mode is continuously checked at step 44 for out of range data. If the inputted data at 44 reveals that an out of range condition has occurred, the control computer 28 transmits an "OUT OF RANGE CONDITION" 45 alarm to the operator. This alarm will serve to stop the current operation for the batch then being processed.

The next block number 46 of FIG. 6, checks for the start of coagulation by the level of the milliamp signal from the differential amplifier 27. The LKSv data value 31 of FIG. 5 represents a preset value of broken line 35 in the control computer 28. The preset value 35 will typically range between 15 and 25 percent of the maximum milliamp output of amplifier 27 in a cheese making process. The intersect 31 of broken line 35 onto profile 5 of FIG. 5 represents commencement of the coagulation by the rennet. The alarm timer value is stored in the control computer 28 memory at 47 for later use and override in the run mode of FIG. 7. The stored alarm timer value of 47 is later used for detecting possible run mode problems and timely alerting the operator of an impending processing problem.

The right vertical column of FIG. 6 includes the step of indexing or programming the learn mode by the cheese maker operator for what the cheese maker observes or considers to be the desired optimum processing stage for cutting the cheese coagulum. At the desired curding point 34 as observed by the cheese making operator, the operator will input to the control computer 28 the correct cutting point 34 at block 48. The current analog signal from the sensor probe is then subtracted from the previously read analog signal at 49 to give a value which represents the rate of coagulation or slope of the coagulation curve as shown in FIG. 5. This value is stored at 50 in the control computer 28 and is used for comparison during run mode operation to determine the correct cutting point 34 in the ensuing subsequent production runs. The alarm elapse time of 47 is also stored and used for error checking during the run mode. The control computer 28 now checks at 52 for the operation of the vat cutters. The learn mode is set and completed at 53 for successful operation and adaptation to the run mode of FIG. 7.

FIG. 7 depicts a flow chart for control computer 28 operating in the run mode and programmed to the learn mode of FIG. 6. This run mode may be used by the computer 28 to automatically engage motors 9 and blades 4 to cut the cheese coagulum at the already indexed optimum cutting point 34. This cutting point 34 has been previously learned and indexed by the cheese maker in the learn mode as the desired predetermined change 34 which allows even the most inexperienced operator conducting the cheese process under the run mode to make consistently accurate cuts. The run mode is selected by the operator at step 60 with step 61 scanning the memory means to detect if the learn mode of FIG. 6 has been successfully completed. The next step 62 awaits for the novice operator to add the rennet to the vatted milk and the alarm timer is then reset at 63. The alarm timer is then started at 64.

Thermal conductivity data (as milliamp input) of the rennet coagulating milk is sent to control computer 28 which reads and compares the inputted data to the stored data from the FIG. 6 learn mode. The inputted data is continuously checked at number 65 for out of range data at block 66. When a sensor out of range 66 reading has occurred, the control computer will send an "OUT OF RANGE CONDITION" 66 alarm to the operator. This alarm will stop the current operation for this batch.

The next block number 67 of FIG. 7 represents reading and comparing inputted data which checks for the start of coagulation by the level of the milliamp signal from the differential amplifier 27. The LKSv data value 31 from FIG. 5 is a preset value 35 in the control computer 28. This preset value 35 typically ranges between 15 and 25 percent of the maximum milliamp outputted by amplifier 27 in the coagulation process. The milliamp units scaled onto the milliamp outputs of FIGS. 5 and 8 represent the percentage of maximum output expressed in 10 percent units. The output of amplifier 27 in a typical cheese manufacture will range from about 4 milliamps to a maximum output of about 20 milliamps. Once the level 35 is detected, values greater than this number 35 level are representative of a commencement of the coagulation. The alarm elapse time from the alarm timer process value is checked at 68 by the control computer 28 to verify that the start of coagulation has occurred within the time window 36. If the start of coagulation has occurred outside of the alarm time window 36, a "START OF COAGULATION ERROR" alarm at 69 will be generated to alert the operator and the run mode operation will be canceled.

The control computer 28 will now continuously comparatively read the current analog signal as subtracted from the previously read analog signal in block 70 for the desired predetermined change (34) as represented by the rate of coagulation of the coagulation curve as shown in FIG. 5. This number is then compared with the LCp number previously stored during the learn mode as shown in block 71 to determine the proper cut point 34. The comparison may involve a comparison of the curved slope and the learned cut point 34 with the batch being processed by the run mode. When the rate of coagulation (e.g. slopes about 34) of the then processing batch (run mode) indexes upon the activating threshold of learn mode (e.g. slope about 34 in learn mode), the run mode is activated for initiating the responsive signal for starting motors 9 and cutters 4. Once the cut point 34 has been detected, the alarm timer is now checked at 72 by the control computer 28 to verify that the start of cut point 34 has occurred within the alarm time window 37 of FIG. 5. If the start of cut point 34 has occurred outside of the alarm window 37, a "CUT POINT ERROR" alarm 73 will be generated to alert the operator and the run mode operation will be halted. The control computer 28 will now start motors 9 and cutters 4 provided no alarms have occurred during this run mode batch. This will complete the run mode for this batch.

The present invention may utilize a variety of different profiles 5 to initiate a responsive signal to a predetermined change in a coagulating liquid. The profile 5a of FIG. 8 depicts another embodiment wherein the vertical line represents a profile 5a adapted for inputting and outputting to the learn and run modes of FIGS. 6 and 7. In FIG. 8, the milliamp output of convertor 27 to computer 28 may be programmed to ascertain the rate at which the inputted milliamp increases during the coagulation process. During the initial processing stages, the milliamp output rate will not appreciably increase until after the rennet addition at 31 starts to coagulate the milk. Commencement of the rennet coagulation of the milk as represented between points 31 and 33 causes a rapid projection or growth of profile 5a of FIG. 8. As the coagulation approaches the indexed cutting point 34, the rate of growth or propagation of points towards maximum output along profile 5a will substantially decrease in rate until the run mode rate will substantially equal that of the learn mode rate.

The learn mode and run mode for profile 5a represented by FIG. 8 may be programmed in the same manner as the representation of FIG. 5 with the rate of propagation or advance towards maximum output rather than slope being the determinative factor for indexing the computer means with the appropriate point 34 to curd the cheese coagulum. Other profiles representing different processes and conditions may likewise be incorporated into the method of this invention.

Control unit 28 is equipped with a conventional operator interface (not shown) which enables the operator to input pertinent processing data or parameters such indexing at learn mode 48 the optimum stage for curding the cheese, alarm processing irregularities such windows or processing cross checking 35 (e.g. rennet addition check at 42 of FIG. 6 and 62 of FIG. 7), and 37 (step 72 of run mode), and alarm and stop systems such as for excessive time elapses throughout the process. The computer 28 is also coupled to standard associated equipment and accessories (not shown) such as for inking and recording the processing data for each run and relaying computerized command responses to signaling alarms, processing terminator switching, stirring and cutting systems of the process, etc.

In the present method, the learn mode is preferably conducted for purposes of establishing in a memory means a processing profile representative of accumulated processing data representative of the liquid converting to a solid and vice versa. The profile establishes the processing parameters of a typical process. After having established stored information of a typical process, the stored information is then run to index upon the profile the desired predetermined change for signaling.

The following example is illustrative of the adaptation of the invention to a cheese manufacture.

EXAMPLE

A conventional cheese vat 1 of the type disclosed in FIG. 1 with a 50,000 pound liquid milk capacity was filled with warm whole milk and maintained for coagulation to cheese at 90°-104° F. The vat 1 was equipped with reversible agitators 4 which served when operated in one direction to agitate the milk in reverse by motors 9 to cut or curd the cheese coagulum. The stir or cut cycling may be appropriately programmed into the learn mode for automation in the run mode.

The thermal conductivity data was obtained by using the Model 8-66 MPS probe assembly 3 as described supra with the transformer being removed therefrom. The probe assembly 3 was connected to a 24V DC power source, differential amplifier 27 and control computer 28 as described above and the circuitry of FIG. 4. During the filling, the milk was continuously agitated so as to prevent milk fat separation. Conventional levels of calcium chloride, a cheese coloring additive and starter were added while filling vat 1 with milk. After filling vat 1 with the whole milk, a coagulating amount of rennet is then added and probe assembly 3 engaged to proved data concerning the thermal conductivity of the milk coagulating to cheese.

The learn mode programming of computer 28 as outlined by the flow sheet of FIG. 6 receives and stores information concerning the conversion of the milk to cheese. The learn mode programming is assisted by an expert cheese maker who made the necessary empirical observations for determining the optimum cutting point 34 and indexing upon the thermal conductivity profile 5 (e.g. depicted in FIG. 5). The minimum and maximum milliamp output by amplifier 27 ranged from about 4 milliamps to about 20 milliamps.

The electrical outputs from resistors 24 and 25 of FIG. 4 were adjusted to a value of 10 percent over zero output by the differential amplifier 27 by adjustment of variable resistor 26 with the probe in an uncoagulated solution. While conducting the learn mode, the necessary processing steps of 40-47 of FIG. 6 were conducted and inputted by operator interface to the control computer 28. The cheese maker (by physically observing and touching the cheese coagulum) determines during the optimum cutting point 34 for curding the cheese which empirical cutting point 34 was inputted into the computer at step 48 of the learn mode of FIG. 6. Blades 4 are reversed by computer 28 signal to commence the curding or cutting of the cheese. The remaining steps of FIG. 6 were sequentially performed and inputted into the control computer 28. The input to computer 28 for the learn mode profiled in FIG. 5 including the initial coagulation point 31, the point 36 Window for determining whether the commencement of coagulation occurs within the windowed region between the broken lines bridging 36 and the optimum cutting point 34 by the cheese maker occurs with broken line region of 37 stored in memory for future use as a warning signal provide processing controls of future production runs monitored and controlled by the run mode.

The curded cheese was then processed in a conventional manner to a cheese product. The manufacturing equipment was cleaned and readied for another plant run using the run mode to determine the optimum cutting point 34.

The run mode batch was conducted in accordance with the sequential procedure described and the flow sheet of FIG. 7. Cheese made pursuant to the run mode with reliance upon the run mode to compare inputted data and automatically initiate cutting upon achievement of cutting point 34 compared favorably with cheese made under the learn mode procedure using an expert cheese maker to index the inputted data and empirically determine the optimum cheese cutting stage. The run mode provided excellent replication of cheese quality to texture, body, flavor and that produced by conventional cheese making processes. The run mode effectively determines and initiates the command signal for automatically starting cutters 4 to curd the cheese coagulum.

What is claimed is:

1. A method for initiating a responsive signal to a predetermined change of a solidifying liquid converting from a liquid to a solid in a subsequent liquid solidification process, said method comprising:
   a) storing in a memory unit at least one thermal conductivity profile of the solidifying liquid;
   b) indexing upon said profile by physical observation an activating threshold indicative of said predetermined change;
   c) conducting the subsequent liquid solidification process while sending thermal conductivity data of said subsequent liquid solidification to the memory unit;

d) comparing said profile to said data in said memory unit until said data reaches the activating threshold; and e) initiating the responsive signal upon achievement of said threshold and thereby initiate said responsive signal to said predetermined change in said subsequent liquid solidification process.

2. The method according to claim 1 wherein the solidifying liquid comprises coagulating milk to a cheese coagulum in a cheese manufacture.

3. The method according to claim 2 wherein said predetermined change represents an optimum stage for cutting the cheese coagulum.

4. The method according to claim 1 wherein the storing of the profile and indexing of the profile with the activating threshold are stored and indexed in a learn mode of the memory unit with said learn mode including stored processing parameters for monitoring the subsequent solidification process.

5. The method according to claim 4 wherein the solidification process comprises coagulating milk to a cheese coagulum in a cheese manufacture.

6. The method according to claim 5 wherein the activating threshold represents an optimum processing stage for cutting the cheese coagulum as observed by a cheese maker and indexed in said learn mode.

7. The method according to claim 6 wherein the method includes in the memory unit an operational run mode wherein the data of the subsequent solidification process of the coagulating milk is compared to the processing parameters of the stored learn mode while operating in the run mode and upon reaching the activating threshold the memory unit initiates the responsive signal to an automated cutting means for automatically cutting the cheese coagulum.

8. The method according to claim 1 wherein the method includes inputting upon said profile an alarming means for alarming an operator of the subsequent process if the subsequent processing data, when compared to said profile, reveals the subsequent data fails to substantially comply with said profile.

9. The method according to claim 2 which includes means for deriving the thermal conductivity profile and said thermal conductivity data by a comparative heat sensing assembly comprised of a heating unit for heating the coagulating milk, a reference heat sensor distally removed from said heating unit for sensing temperature of the coagulating milk, and an active heat sensor for absorbing undissipated heat about said heating unit as the coagulating milk converts to the cheese coagulum.

10. The method according to claim 9 wherein the means for deriving includes electronic outputs derived from a wheatstone bridge arrangement in which the active heat sensor and the reference heat sensor are opposingly positioned so as to provide an unbalanced path of electrical resistance for current flowing through said active heat sensor and reference heat sensor when the milk converts to the cheese coagulum.

11. The method according to claim 3 wherein the storing of the profile includes relaying to the memory unit thermal conductivity inputs of a first milk mass converting to a first cheese coagulum in a cheese manufacture and the physical observation for indexing the predetermined change to said profile is made by empirically observing the optimum stage for cutting the cheese coagulum.

12. The method according to claim 9 wherein the subsequent process of coagulating milk to cheese includes inputting thermal conductivity data of the subsequent process and the comparing of the inputted data of the subsequent process to the stored profile in said memory unit and initiating means associated to said memory unit for automatically engaging cheese coagulum cutters to cut the cheese when the compared data of said subsequent process thresholds upon the optimum cutting stage indexed onto said profile.

13. A method for initiating a responsive signal in repeative processes of a common recipe wherein liquid masses are converted to coagulated masses and the responsive signal reflects an achievement of a predetermined processing condition of the processes, said method comprising:

a) inputting sufficient processing data to memory means to establish a processing profile reflective of the predetermined processing condition;

b) indexing the processing profile with an activating threshold reflective of the predetermined condition;

c) conducting a subsequent process wherein by the common recipe a liquid mass converts to a coagulated mass while sending subsequent processing data of said subsequent process to said memory means;

d) comparing in said memory means said profile to said subsequent processing data until said subsequent data achieves the activating threshold of the predetermined processing condition; and e) initiating the responsive signal when said subsequent processing data achieves the activating threshold.

14. The method according to claim 13 wherein the liquid masses converting to the coagulated masses comprise milk converting to a cheese coagulum.

15. The method according to claim 14 wherein the indexing of the activating threshold represents an observed optimum stage for cutting the cheese coagulum.

16. The method according to claim 14 wherein the inputting sufficient processing data and indexing of the profile with the activating threshold are stored and indexed in a learn mode of the memory means with said learn mode including stored processing parameters for monitoring subsequent coagulating processes of the milk converting to the cheese coagulum.

17. The method according to claim 16 wherein the method includes in the memory means an operational run mode wherein the data of the subsequent coagulating process is compared to the processing parameter of the stored learn mode and the memory means initiates the responsive signal to an automated cutting means for automatically cutting the cheese coagulum.

18. The method according to claim 17 which includes comparative thermal conductivity means for inputting said sufficient processing data and sending said subsequent processing data to said memory means by a comparative heat sensing assembly comprised of a heating unit for heating the coagulating milk, a reference heat sensor distally removed from said heating unit for sensing temperature of the coagulating milk, and an active heat sensor positioned in close proximity to said heating unit for absorbing undissipated heat about said heating unit as the coagulating milk converts to the cheese coagulum.

19. The method according to claim 17 wherein the subsequent process of coagulating milk to cheese includes inputting thermal conductivity data of the subsequent process and comparing the inputted data of the subsequent process to the stored profile in said memory means and initiating means associated to said memory means for automatically engaging cheese coagulum cutters to cut the cheese when the compared data of said subsequent process thresholds upon an optimum cutting stage indexed onto said profile.

20. The method according to claim 18 wherein the comparative thermal conductivity means includes electronic outputs derived from a wheatstone bridge arrangement in which the active heat sensor and the reference heat sensor are opposingly positioned so as to provide an unbalanced path of electrical resistance for current flowing through said active heat sensor and reference heat sensor as the coagulating milk converts to the cheese coagulum, and the electronic outputs of said arrangement are converted by a convertor to a milliamp output for inputting to said memory means.

* * * * *

REEXAMINATION CERTIFICATE (2896th)
United States Patent [19]
Weber et al.

[11] B1 5,273,765
[45] Certificate Issued May 28, 1996

[54] INITIATING A RESPONSE SIGNAL TO A PREDETERMINED PROCESSING CONDITION

[75] Inventors: Mark J. Weber, Marshfield; Marc A. Winzenried, Dorchester, both of Wis.

[73] Assignee: ESE, Inc., Marshfield, Wis.

Reexamination Request:
No. 90/003,745, Mar. 3, 1995

Reexamination Certificate for:
Patent No.: 5,273,765
Issued: Dec. 28, 1993
Appl. No.: 16,050
Filed: Feb. 10, 1993

[51] Int. Cl.$^6$ .................................................. G01N 25/00
[52] U.S. Cl. ........................ 426/231; 73/64.41; 426/36; 426/233
[58] Field of Search ..................... 426/231, 233, 426/36, 582; 73/64.41; 374/16

[56] References Cited

U.S. PATENT DOCUMENTS

| | | | |
|---|---|---|---|
| 3,366,942 | 1/1968 | Deane | 340/243 |
| 3,453,864 | 7/1969 | Chiu | 73/15 |
| 3,821,643 | 6/1974 | Bostick et al. | 324/65 R |
| 3,840,806 | 10/1974 | Stoner et al. | 324/65 R |
| 3,898,638 | 8/1975 | Deane et al. | 340/243 |
| 3,899,595 | 8/1975 | Stenne | 426/36 |
| 4,059,006 | 11/1977 | Mizutani et al. | 73/17 A |
| 4,244,217 | 1/1981 | Ledbetter | 73/204 |
| 4,484,821 | 11/1984 | Willcock | 374/24 |
| 4,501,145 | 2/1985 | Boegli et al. | 73/204 |
| 4,512,182 | 4/1985 | Rizvi et al. | 73/64 |
| 4,542,645 | 9/1985 | Richardson et al. | 73/64.1 |
| 4,578,988 | 4/1986 | Hori et al. | 73/54 |
| 4,611,928 | 9/1986 | Hori et al. | 374/21 |
| 4,663,169 | 5/1987 | Hori et al. | 426/38 |
| 4,781,469 | 11/1988 | Turon-Lagot | 374/27 |
| 5,014,553 | 5/1991 | Hori et al. | 73/295 |
| 5,064,294 | 11/1991 | Cerf et al. | 374/16 |

OTHER PUBLICATIONS

Journal of Food Science, 48 (5): 1492–1496.

*Primary Examiner*—George Yeung

[57] ABSTRACT

The present invention provides a method for initiating a responsive signal to a predetermined processing condition. The method relies upon generating sufficient processing data about a desired processing condition to establish a processing profile reflective of the condition. The predetermined processing condition is indexed or inputted onto the profile which, in turn, allows for automatically initiating the signal when subsequent processes achieve the indexed condition. The method is particularly applicable for determining a proper curding point in a cheese manufacture using a control computer to store and compare an indexed processing profile with an on-going plant run.

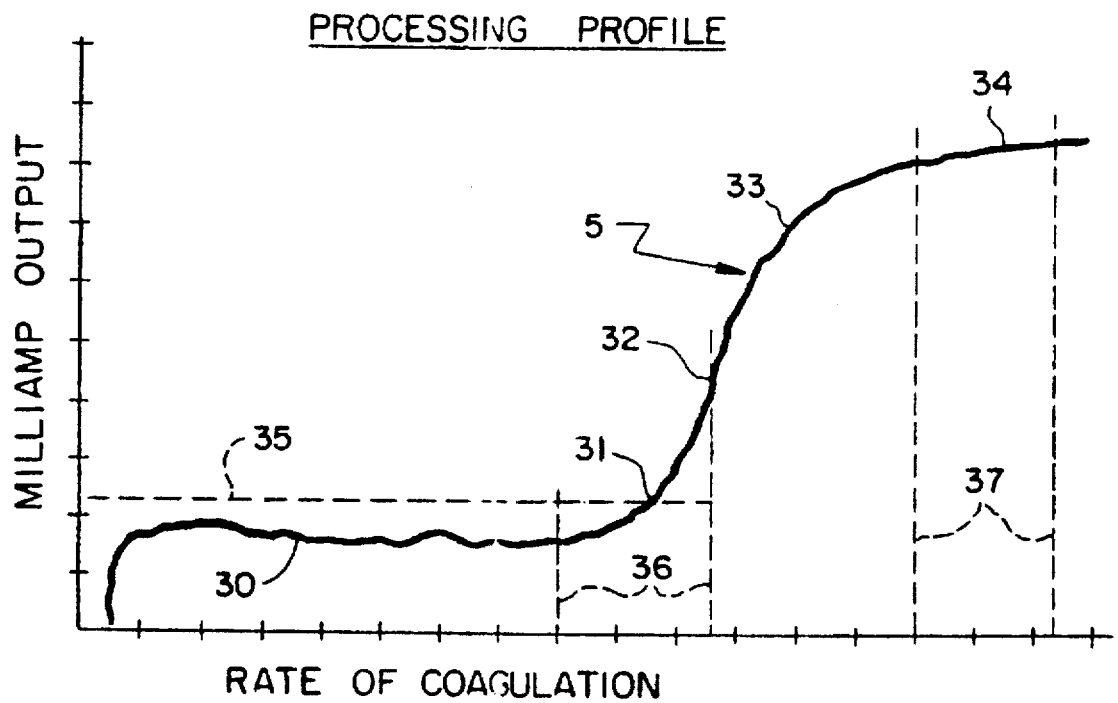

B1 5,273,765

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–20 are cancelled.

* * * * *